US00PP09436P

United States Patent [19]

Konta

[11] Patent Number: Plant 9,436

[45] Date of Patent: Jan. 23, 1996

[54] 'HAKKO' CHERRY TREE

[76] Inventor: Koichiro Konta, No. 131, Ooaza Dai, Kahoku cho, Nishi murayama gun, Yamagata pref., Japan

[21] Appl. No.: 337,458

[22] Filed: Nov. 4, 1994

Related U.S. Application Data

[63] Continuation of Ser. No. 202,700, Feb. 25, 1994, abandoned, which is a continuation of Ser. No. 83,333, Jun. 29, 1993, abandoned, which is a continuation of Ser. No. 688,781, Apr. 16, 1991, abandoned.

[51] Int. Cl.[6] ..... A01H 5/00

[52] U.S. Cl. ..... Plt./37

[58] Field of Search ..... Plt./37

[56] References Cited

U.S. PATENT DOCUMENTS

P.P. 41 11/1932 Burbank ..... Plt./37

*Primary Examiner*—James R. Feyrer

*Attorney, Agent, or Firm*—Armstrong, Westerman, Hattori, McLeland & Naughton

[57] ABSTRACT

The cherry variety Hakko is selected from seedlings of Sato Nishiki crossed with Jabouley. It has few flowers per inflorescence, a high fruit set, and large fruit with an overall vividred color substantially covering a light yellow ground, light and inconspicuous surface speckling, and a pale yellow flesh color which turns progressively translucent with ripening.

4 Drawing Sheets

This application is a continuation application of application Ser. No. 08/202,700 filed Feb. 25, 1994, which was a continuation of application Ser. No. 08/083,333, Jun. 29, 1993, which was a continuation of application Ser. No. 07/688,781, filed Apr. 16, 1991, all now abandoned.

BACKGROUND OF THE INVENTION

The cherry variety of this invention was selected and developed by Koichiro Konta in Japan from 86 seedlings of Sato Nishiki crossed with Jabouley (early Lyons) in 1961. Sato Nishiki is a popular Japanese variety of cherry bred in Japan, and was originally selected from seedlings of Napoleon crossed with Governor Wood. In 1967, the inventor selected one seedling of the cherry variety of this invention which had good and large fruit. His observations over 5 years from the first crop indicated that the seedling had the desirable characteristics of early flowering, good tree performance in terms of flower numbers and excellent fruit with good color.

Accordingly, he grafted the variety of this invention on a Napoleon tree and on an Aoba rootstock for confirmation of stability. This grafting took place at:
No. 1125-1, Kawamukai Tanakajima,
Ooaza Dai, Kahoku-cho,
Nishimurayama-gun, Yamagata, Japan The variety of this invention grafted on Napoleon and on Aoba expressed the same characteristics as the mother tree. Those characteristics are described herein, all specific color descriptions being by reference to the ISCC — NBS system.

BRIEF DESCRIPTION OF THE DRAWINGS

The accompanying drawings illustrate the variety Hakko and the characteristics of its fruit.

SUMMARY OF THE INVENTION

Figure 1:
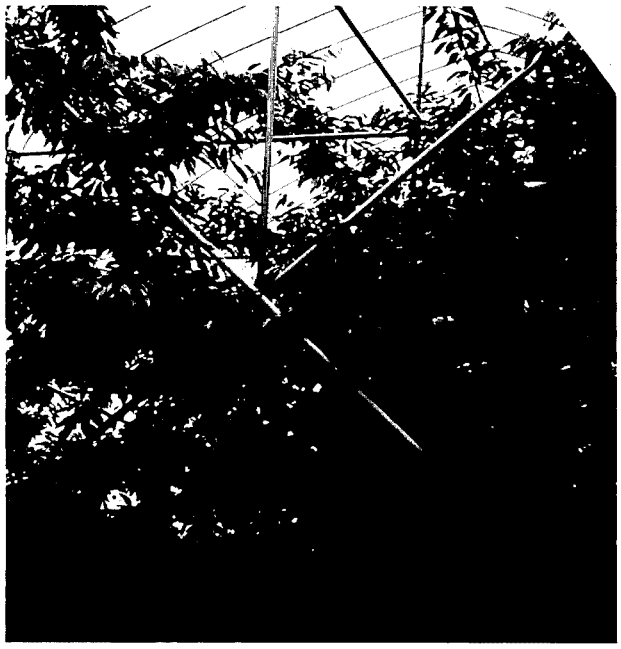
FIG. 1 is a photograph of Hakko fruit on the original tree.
Figure 2:
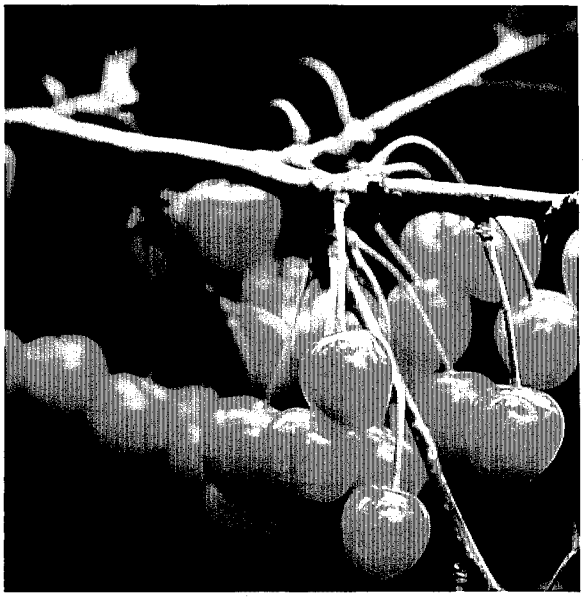
FIG. 2 is a photograph of Hakko fruit on the tree.
Figure 3:
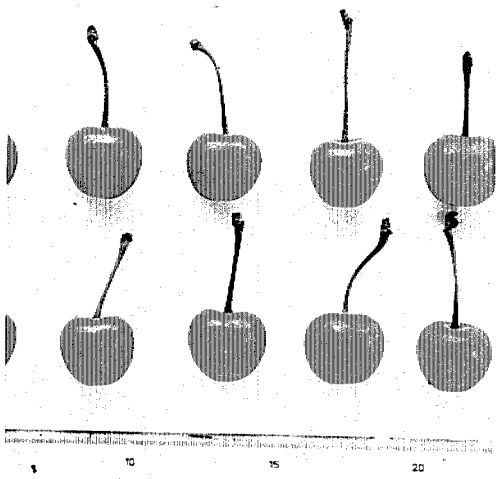
FIG. 3 is a photograph of Hakko fruit (side view)
Figure 4:
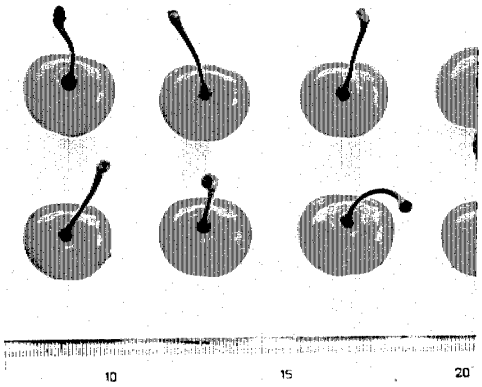
FIG. 4 is a photograph of Hakko fruit (from stem end)
Figure 5:
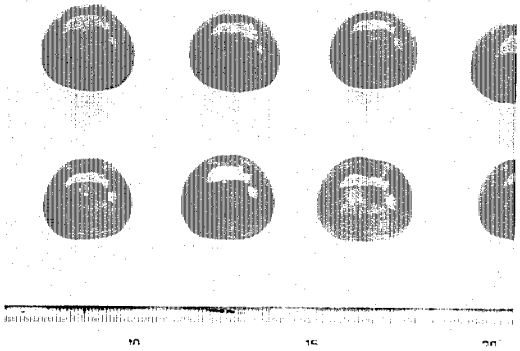
FIG. 5 is a photograph of Hakko fruit (opposite from stem end)
Figure 6:
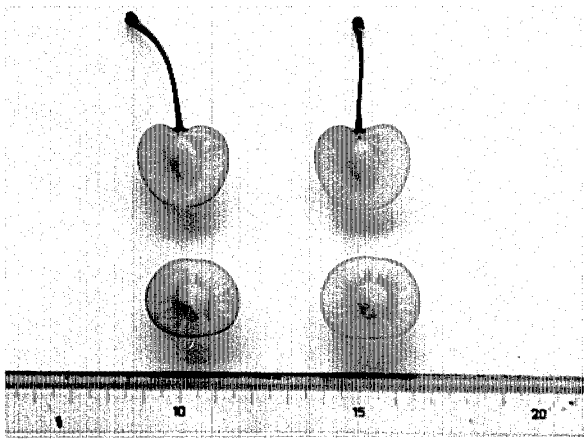
FIG. 6 is a photograph of cross sections of Hakko fruit.
Figure 7:
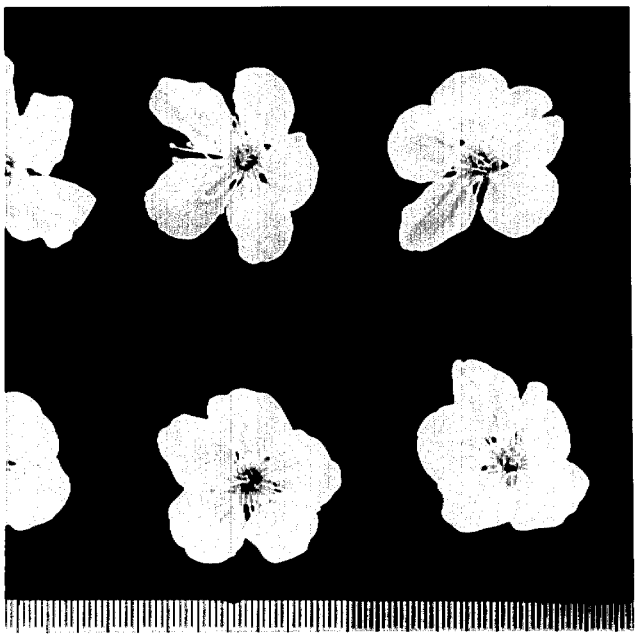
FIG. 7 is a photograph of Hakko flowers (top view)
Figure 8:
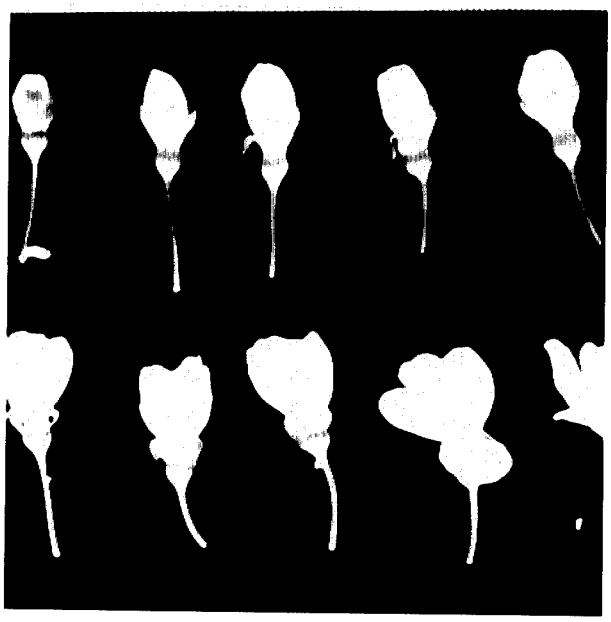
FIG. 8 is a photograph of unopened Hakko flowers (side view)
Figure 9:
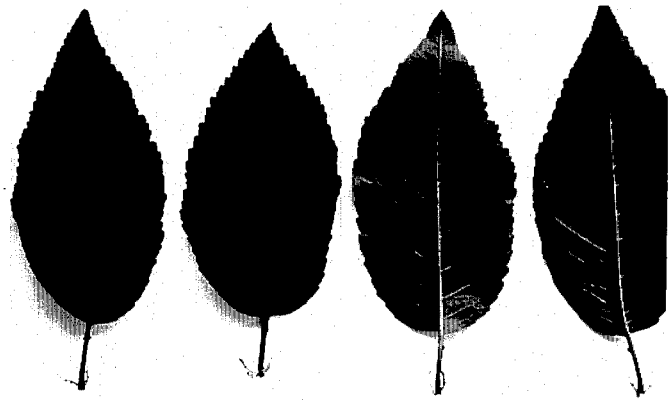
FIG. 9 is a photograph of Hakko leaves.

The variety Hakko was selected from seedlings of Sato Nishiki crossed with Jabouley. The fruit is heart-shaped and medium to slightly big (average 7 g). It ripens for harvest beginning about June 20 on the original tree at Kahoku-cho, Yamagata, Japan. The tree is spreading, of medium size and somewhat vigorous. The shoot is thin and long, of moderate brown color. The leaf is oval and of medium size. The tree has a showy flowering and has few large flowers with oblong and large petals, strong yellow green sepal and medium peduncle. The bud is slightly rounded. The fruit is of medium size, flat heart-shaped with a shallow concave apex, and a shallow and narrow stalk cavity. The skin is glossy and smooth, vivid red overall on a light yellow ground. The flesh is pale yellow without arthocyanin coloring of the flesh and around the stone, and has a medium sweetness and little acidity. The stone is elliptical, of medium size and semi-adherent.

Sprouting, leafing and flowering are early. The fruit is harvested in mid to late June, 2–3 days earlier than Sato Nishiki. This variety has medium productivity, medium cracking tendency and keeping quality. Hakko is distinguished from Rockport Bigarreau by the shorter vertical length of its fruit, slightly harder flesh, smaller stone and redder skin. Further, it is distinguished from Sato Nishiki by an earlier flowering time (1–2 days earlier), fewer flowers per cluster, shallow fruit apex, redder skin, and a thin shoot which has more red in its color.

Breeding History of the Variety (1) Denomination:
*Mother variety.*—Sato Nishiki.
*Father variety.*—Jabouley.

(2) Place of breeding:
No. 1125-1, Kawamukai Tanakajima,
Ooaza Dai, Kahoku-cho,
Nishimurayama gun, Yamagata, Japan.

(3) Purposes of breeding program: To breed excellent mid-season sweet cherry with good color and stable productivity.

Process of Breeding

The inventor sowed seeds of Sato Nishiki crossed with Jabouley in 1961. He grew 86 seedlings in the next year. Six years later, he selected one seedling with good color and big fruit. He observed its characteristics for growth and fruit over 5 years. As a result, he confirmed that the variety has the desirable characteristics of early sprouting, leafing and flowering, vigorous tree, high fruit set in comparison to flowers per cluster, good fruit color and good quality. He grew the variety under adequate growth conditions. In 1983, he grafted the variety on a Napoleon (Royal Ann) tree and the next year on an Aoba rootstock. These trials indicated that the characteristics of the tree on Napoleon and Aoba are the same as those of the mother tree.

Trials for Determining Characteristics (1) Trials Procedure a. Place of trials:
No. 1125-1, Kawamukai Tanakajima,
Ooaza Dai, Kahoku-cho,
Nishimurayama-gun, Yamagata, Japan.
b. Dates and periods of trials: April 1988–July 1989.
c. Name of control varieties: Sato Nishiki; Rockport Bigarreau.
d. Brief description of trials: The inventor planted the original tree, 27 trees (1 year-old), 3 trees (6 year-old) and 13 trees (4 year-old) on his level orchard with sod culture. He fertilized with 1.25 kg/hectare of fertilizer mainly composed of organic, humus barnyard manure. Trees are typically covered by a plastic house to protect from rainfall cracking.

(2) Result of Trials

Hakko breaks dormancy about 1–2 days earlier than Sato Nishiki in the spring, flowering about 1–2 days earlier. In comparison to other commercial cherry varieties of the area, this tree would be regarded as having fewer flower buds and fewer flower buds per flowering spur and fewer flower buds at non-spurred flowering nodes. However, while this tree produces fewer flowers when compared to most other commercial comparison trees, productivity remains sufficiently high because this tree has a comparatively high level of fruit set to the number of flowers presented. The resulting fruit attains an advantageously large size without the fruit having to be thinned, as may be required with comparison varieties which have a higher level of flower bud production and higher levels of fruit set. Fruit size is typically larger than that of Sato Nishiki, which may need thinning. This tree produces abundant pollen and is cross-compatible with Sato Nishiki, which serves as an excellent pollinator for Hakko.

The fruit of Hakko begins to color from late May, and matures to a bright red at maturity, but before full ripeness. Fruit ripening of Hakko is slightly earlier or with Sato Nishiki. Harvest is typically about 45 days from full bloom for this tree. Fruiting branches may weep with fruit loads due to the high vigor and consequent thin twigs of this variety. Current season's growth typically abundantly branches in spreading patterns, and renders numerous rounded, large flower buds which break the following season. Foliage, even on basal stem portions, remains green until leaf fall after first frost which normally occurs in about early November.

Main use of the variety: Dessert sweet cherry.

Cultivation:

(1) *Regions appropriate for cultivation.*—All areas.
(2) *Type of cropping.*—For growing under vinyl house for protection from rain.
(3) *Suggestions useful for cultivation.*—Hakko is highly vigorous. Training and pruning should be selected to discourage prolific growth. Because fruit reaches full color before ripeness, care should be taken to avoid harvest of fruit before full ripeness is attained.

Botanical Description of the Claimed Plant

Tree: Tree is spreading, of medium size and strong vigor.

Shoot: Shoot is of medium thickness (diameter 0.43 cm), more thin than Sato Nishiki and Rockport Bigarreau. Color is moderate brown, more red than Sato Nishiki and Rockport Bigarreau. Internode in medium (4.5 cm), longer than in Sato Nishiki and Rockport Bigarreau. Shoot has many large, dense lenticels. Dormant shoot is covered with light grayish yellow brown wax on moderate brown ground color, more red than Sato Nishiki and Rockport Bigarreau. Lenticels are medium size and round with a deep orange color. Bud is blunt-shaped.

Leaf: Leaf is oval, dark olive green and medium size (length 14.7 cm, width 6.6 cm), with narrow and small stipules. Leaf gland is reniform. Two reniform glands on petiole or on base of leaf blade are small (about 2.14 mm with anthrocyanin coloration).

Flower: Flower has a medium number of petals and is of a large size (diameter 3.3 cm). There are few florets per cluster. Petals are large (width 1.6 cm, length 1.2 cm), ovate, and yellowish white. Flower is fertile and has one pistil. Stamen is yellowish white and pollen is present. Calyx tube is bell-shaped. Calyx is strong yellow green. Sepal is medium length. Peduncle is medium length (1.7 cm). Florets in flower cluster are few (average of 2.2 florets per cluster); therefore, fruit grows large without fruit thinnings.

Fruit: Fruit is medium size (7.5 g), flat round, shallow concave apex (length 2.3 cm, width 2.5 cm, thickness 2.1 cm), with shallow and narrow stalk cavity (depth of stalk cavity 1.93 mm; width of stalk cavity 11.38 mm). Skin is vivid red over all on a light yellow ground, wtih inconspicuous surface speckling. Stalk is 4.3 cm. Flesh is medium soft and pale yellow without anthrocyanin coloration in flesh and on surface of stone. Flesh color turns progressively translucent with ripening. Flesh is medium in acidity, sweetness and juiciness. Juice of flesh is substantially clear, not colored. Skin starts to color in late May. Sugar content (Brix) of flesh is 16.0, pH is 3.56. Flesh is juicy, but not bitter or astringent. Firmness of flesh is medium, similar to Napoleon. Fruit dot on skin is very small and light yellow.

Stone: Stone is elliptical, medium size (0.4 g), and smaller than for Rockport Bigarreau. It is semi-adherent to the flesh and is a pale yellow color. Surface of the stone is smooth. Length of the stone is 1.2 cm, width is 0.8 cm, and thickness if 1.0 cm.

Flowering time: Flowers 1–2 days earlier than Sato Nishiki. Beginning of flowering is April 28 and flowers are in full bloom on May 1st.

Maturing time: Fruit picks in mid to late June on original tree, 2–3 days earlier than Sato Nishiki. Fruit matures in 41–50 days.

Pollination: The variety of this invention is fertilized by the pollen of Sato Nishiki (fertility of 27.2%), and Sato Nishiki is fertilized by the pollen of the variety of the present invention (fertility of 27.5%).

I claim:

1. A new and distinct variety of cherry tree, substantially as illustrated and described herein, particularly characterized by producing medium to large fruit of a vivid red color and an earlier flowering time than the known "Sato Nishiki" variety of cherry tree.

* * * * *